United States Patent
Zich et al.

(10) Patent No.: US 9,238,777 B2
(45) Date of Patent: Jan. 19, 2016

(54) METHOD FOR PRODUCING PHOSPHORUS-CONTAINING FLAME RETARDANTS

(71) Applicant: Metadynea Austria GmbH, Krems (AT)

(72) Inventors: Thomas Zich, Linz (AT); Fritz Johann Freidl, Krems (AT); Bernadette Mehofer, Krems (AT); Manfred Doring, Worth Am Rhein (DE); Michael Ciesielski, Merseberg (DE); Bettina Burk, Darmstadt (DE)

(73) Assignee: METADYNEA AUSTRIA GmbH, Krems (AT)

( * ) Notice: Subject to any disclaimer, the term of this patent is extended or adjusted under 35 U.S.C. 154(b) by 0 days.

(21) Appl. No.: 14/633,156

(22) Filed: Feb. 27, 2015

(65) Prior Publication Data

US 2015/0203759 A1 Jul. 23, 2015

Related U.S. Application Data

(63) Continuation of application No. PCT/AT2013/050167, filed on Aug. 28, 2013.

(30) Foreign Application Priority Data

Aug. 29, 2012 (AT) .................................. A 944/2012

(51) Int. Cl.
*C07D 251/66* (2006.01)
*C07F 9/44* (2006.01)
*C07F 9/6521* (2006.01)
*C07F 9/6574* (2006.01)
*C09K 21/12* (2006.01)
*C07F 9/6571* (2006.01)

(52) U.S. Cl.
CPC ............... *C09K 21/12* (2013.01); *C07D 251/66* (2013.01); *C07F 9/44* (2013.01); *C07F 9/4476* (2013.01); *C07F 9/65217* (2013.01); *C07F 9/657154* (2013.01)

(58) Field of Classification Search
CPC ........ C07F 9/44; C07F 9/4476; C07D 251/66
USPC .......................................................... 544/195
See application file for complete search history.

(56) References Cited

U.S. PATENT DOCUMENTS 6,797,821 B2 * 9/2004 Wang et al. .................. 544/195
2005/0004339 A1    1/2005 Wang et al.

FOREIGN PATENT DOCUMENTS

| CN | 102190801 A | 9/2011 |
| DE | 2034887 A | 1/1972 |
| JP | 812692 A | 1/1996 |

OTHER PUBLICATIONS

Schäfer et al., J. Appl. Polym. Sci 105(2) pp. 685-696 (2007).
International Search Report PCT/AT2013/050167 issued on Dec. 11, 2013.

* cited by examiner

*Primary Examiner* — Venkataraman Balasubramanian
(74) *Attorney, Agent, or Firm* — Hoyng Monegier LLP; Ramin Amirsehhi

(57) ABSTRACT

A method for producing compounds of formula (I) in which the radical $R^1$ is selected from $-NH_2$, $-NH_{2-z}Az$, and monovalent alkyl and aryl radicals, the radicals A are selected in each case independently of one another from the phosphoryl radicals DOPO-, DPhPO- and DPhOPO-, and the indices x, y and z, in each case independently of one another, stand for 0 or 1, wherein at least one of the indices is ≠0, by reacting, in a first step, melamine or, when $R^1$ is an alkyl or aryl radical, the corresponding alkyl or aryl guanamine, with one or more of the corresponding phosphinyl chlorides DOP-CI, DPhP-Cl and DPhOP-CI, in order to bond one or more phosphinyl radicals to the amino groups(s) of the melamine or guanamine, and in a second step oxidizing the phosphinyl radical(s) by reaction with an oxidizing agent to give the corresponding phosphoryl radical(s).

12 Claims, No Drawings

METHOD FOR PRODUCING PHOSPHORUS-CONTAINING FLAME RETARDANTS

CROSS REFERENCE TO RELATED APPLICATIONS

This application is a continuation of PCT application number PCT/AT2013/050167 filed on 28 Aug. 2013, which claims priority from application number A 944/2012 filed on 29 Aug. 2012. Both applications are hereby incorporated by reference in their entireties.

BACKGROUND OF THE INVENTION

1. Field of the Invention

The invention relates to a novel method for producing phosphorus-containing compounds which are effective as flame retardants.

For a long time, phosphorus compounds have been known to be flame retardants. In recent years, they have frequently also included 9,10-dihydro-9-oxa-10-phosphaphenanthrene-10-one or -oxide (DOPO), which was described for the first time by Sanko Chemical Co Ltd in DE 20 34 887, and various derivatives thereof. Their flame retardant properties appear to be due to the release by them of phosphorus-containing radicals when heated (see, for example, Schäfer et al., J. Appl. Polym. Sci. 105(2), 685-696 (2007)).

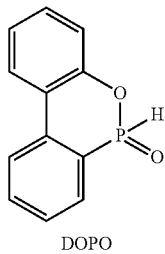

DOPO

Derivatives of diphenylphosphine oxide (DPhPO) and diphenylphosphite (DPhOPO) are also known to be phosphorus compounds with a flame retardant effect; the mode of action is similar.

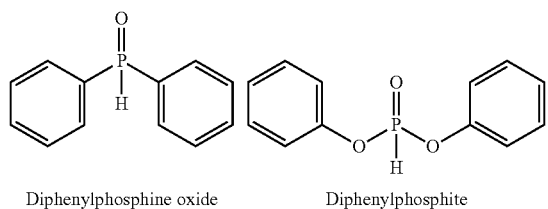

Diphenylphosphine oxide      Diphenylphosphite

On the other hand, melamine and guanamine derivatives are among known nitrogen-containing compounds with a flame retardant effect:

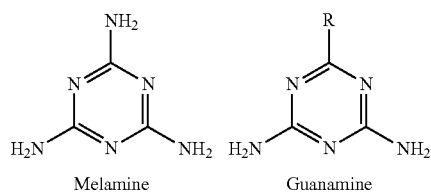

Melamine      Guanamine whereupon experiments were carried out to combine such phosphorus-containing and nitrogen-containing compounds into flame retardants. Attempts were also made to produce covalent compounds between such molecular groups.

In US 2003/120021 A1, which corresponds to U.S. Pat. No. 6,797,821 B2, and US 2005/0004339 A1 from Wang et al., curing agents for epoxy resins or epoxy resins cured therewith are described which each contain one or more DOPO or diarylphosphine oxide groups covalently bonded to nitrogen-containing molecules, including melamine, methyl and phenyl guanamine and have the following formula:

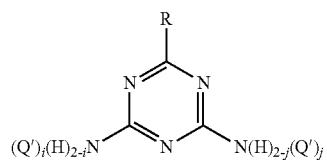

in which Q' could be, inter alia, a DOPO or DPhPO residue, R could be $NH_2$, $CH_3$ or phenyl, and i and j respectively represent 0, 1 or 2. In synthesis examples 13 and 14 of both cited applications, however, only products with the above formula in which i=1 and j=0, i.e. mono-phosphorylated melamine or guanamine, were described, and in fact by reacting 1 mol of DOPO-Cl, i.e. 10-chloro-9,10-dihydro-9-oxa-10-phosphaphenanthrene-10-one, or 1 mol of DPhPO-Cl, i.e. diphenylphosphoryl chloride, with 1 mol of melamine and heating to about 170° C. The analogous synthesis of compounds containing more than one phosphorus-containing DOPO or DPhPO group by reacting i+j mol of Q'Cl with 1 mol of melamine or guanamine was mentioned in general terms without, however, describing a specific method.

During the course of their research, the Applicants have discovered that this analogous reaction of up to 4 mol of DOPOCl or DPhPOCl with 1 mol of melamine or guanamine cannot produce the desired products if i and/or j is/are equal to 2, and in particular if the melamine is only derivatized at two of its three amino groups. Because of the reactivity of the hydrogen of an amino group which has already been monosubstituted with the respective phosphorus compound, i.e. a —NHQ' group, then in theory it is not possible to di-substitute an amino group with Q' without protecting the hydrogens of the third amino group, since —$NH_2$ is much more reactive than —NHQ' as regards phosphoryl chlorides.

Furthermore, the reaction times in Wang et al's method are very long. Thus, for example, once addition of the reagents has been completed, stirring times of 16 h (for DOPO-Cl) or 10 h (for DPhPO-Cl) are necessary in order to obtain essentially complete conversion, even though temperatures of around 170° C. are employed.

Thus, the aim of the invention is to provide an improved method for the production of such or similar compounds by means of which these compounds can be obtained in good yields after relatively short reaction periods and essentially without any disruptive side reactions.

2. Description of the Related Art

The invention accomplishes this aim by providing a method for producing compounds with the following formula (I):

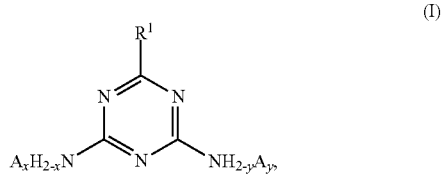

wherein:
the residue $R^1$ is selected from —$NH_2$, —$NH_{2-z}A_z$ as well as monovalent alkyl and aryl residues,
the residues A are each, independently of each other, from the following phosphoryl residues DOPO-, DPhPO- and DPhOPO-:

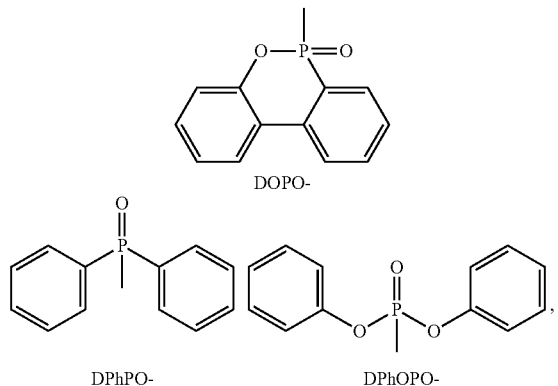

and
the indices x, y and z each, independently of each other, represent 0 or 1, wherein at least one of the indices ≠0;
in which, in a first step, melamine or, when $R^1$ is an alkyl or aryl residue, the corresponding alkyl or aryl guanamine is reacted with one or more of the following phosphinyl chlorides DOP-Cl, DPhP-Cl and DPhOP-Cl:

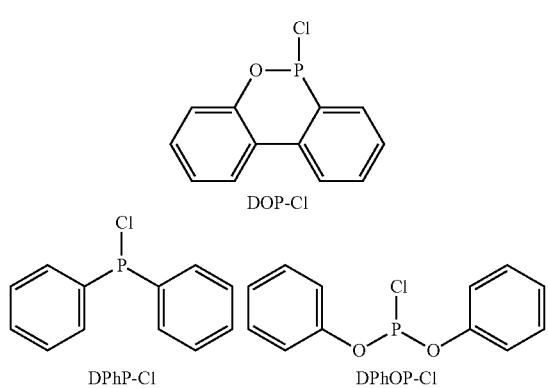

in order to bind one or more phosphinyl residue(s) to the amino group(s) of the melamine or guanamine, after which in a second step, the bound phosphinyl residue(s) is(are) oxidized by reaction with an oxidizing agent to form the corresponding phosphoryl residue(s).

More precisely, in the first step, a compound with formula (II):

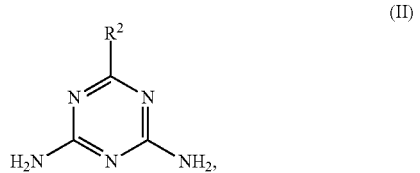

wherein the residue $R^2$ is selected from —$NH_2$ and monovalent alkyl and aryl residues, i.e. melamine or a guanamine, is reacted with one or more of the phosphinyl chlorides DOP-Cl, DPhP-Cl and DPhOP-Cl to form one or more compounds with the following formula (III):

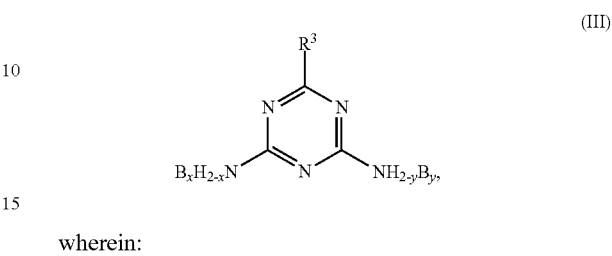

wherein:
the residue $R^3$ is selected from —$NH_2$, —$NH_{2-z}B_z$ and monovalent alkyl and aryl residues;
the residues B, independently of each other, are selected from the following phosphinyl residues DOP-, DPhP- and DPhOP-:

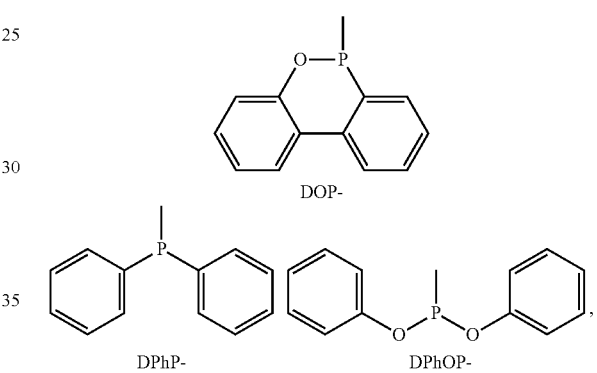

and
the indices x, y and z are as hereinbefore defined;
wherein in the second step, the compound(s) with formula (III) are oxidized by reaction with the oxidizing agent to form one or more compounds with formula (I).

By means of this novel method, not only can compounds with formula (I) be produced in good yields and essentially without side reactions, but also, melamines can be produced which are tri-substituted with the respective phosphorus-containing residue without problems, and specific mixtures of mono-substituted and di-substituted aminotriazines can also be obtained, as will be seen in the examples below. Furthermore, the reaction times compared with Wang et al's method could be substantially reduced, which is of distinct economic advantage having regard to the high reaction temperatures employed.

Without wishing to be bound by a specific theory, it is assumed that this due to the substantially greater reactivity of phosphinyl chlorides compared with the corresponding phosphoryl chlorides. However, the near-quantitative yields for production of the desired compounds was surprising. It is actually because of the high reactivity of the phosphinyl chlorides that more side reactions should have been expected to occur—especially at the preferred high reaction temperatures of up to 200° C. This means that it was unexpected that essentially, the respective desired product would be formed exclusively containing one phosphorus-containing residue per amino group; rather, a certain—albeit smaller—fraction with two phosphorus-containing residues on one amino group would have been expected to have been obtained. However, this latter case was not observed at all. Thus, the phosphinyl chlorides employed in the method of the invention have a sufficiently high reactivity to allow rapid bonding of exactly one phosphorus-containing residue to occur per amino group, but it is not sufficient to di-substitute the amino group, even when a molar excess of phosphinyl chloride is employed.

Furthermore, the phosphinyl chloride DOP-Cl used in the method of the invention for the production of DOPO derivatives is an industrial intermediate in the production of the conventional flame retardant DOPO, and thus is produced in large quantities, and hence is much cheaper and more readily available than the phosphoryl chloride DOPO-Cl which is used in Chun-Shan Wang's method.

The monovalent alkyl and aryl residues as options for the residues $R^1$ to $R^3$ are preferably —$CH_3$ or —$C_6H_5$, i.e. methyl or phenyl, since these form conventional and readily obtainable guanamines—methyl guanamine and phenyl—and also benzo-guanamine. The method of the invention is, however, applicable to a broad range of substituents on the diaminotriazine nucleus, and hence the scope of protection should not be limited to these two preferred residues.

The phosphorus-containing intermediates obtained in the first step are largely stable to hydrolysis and thus can readily be isolated, for example by stirring into water. Furthermore, one-pot syntheses are possible for both steps. Both will be described in the exemplary embodiments below.

There are no particular limits as to the oxidizing agent, as long as it does not result in any unwanted side reactions of the reaction participants. In preferred embodiments, a peroxide is in fact used, as any excesses are easy to separate or destroy. In addition to hydrogen peroxide, $H_2O_2$, many other peroxides and hydroperoxides may be used. Even the oxidation of DOP to DOPO with ozone, which is known from the literature, is possible, but in the inventors' experiments, the results were not as good as with hydrogen peroxide or t-butyl hydroperoxide. Finally, $H_2O_2$ is preferred because of its greater stability and thus ease of handling.

Since HCl is given off in the reaction between phosphinyl chloride and the aminotriazine, the first step is preferably carried out in the presence of an acid scavenger in order to displace the reaction equilibrium towards the product side. The acid scavenger is preferably 1-methylimidazole, although clearly other compounds known to the skilled person, such as ammonia, alkyl- and aryl-amines and other nitrogen compounds such as trimethylamine, pyridine, imidazole and the like, or other bases such as alkali and alkaline-earth metal compounds, for example, may also be used. 1-methylimidazole has the great advantage that its hydrochloride melts at a temperature as low as 75° C. (while, for example, the non-methylated homologue imadazolium chloride has a melting point of 158-161° C.), and thus with a suitable choice for the solvent and the reaction temperature, a second liquid phase which can easily be separated is formed in addition to the reaction solution.

Both steps are preferably carried out in an organic solvent in order to ensure the homogeneity of the reaction and heat dissipation. There are no specific restrictions applying to the solvent, as long as it is chemically inert having regard to the reactions occurring therein and the starting products are soluble or at least dispersible therein. However, in the first step, for the reasons given above, it should have a boiling point which is substantially above 75° C., the DOP-Cl should have a sufficiently good solubility in it, and 1-methylimidazolium chloride should not dissolve in it. In accordance with the present invention, then, a relatively apolar, anhydrous solvent is preferably used, more preferably an aromatic hydrocarbon such as, for example, benzene, toluene, xylene or the like, in particular toluene. Preferably, the same solvent is used both for reaction of the aminotriazine with the phosphinyl chloride and also for the subsequent oxidation. However, different solvents may also be used, for example chloroform for the first step and toluene for the oxidation, etc.

In preferred embodiments of the invention, in the first step, the acid scavenger simultaneously acts as a solvent; hence in particular in this case, 1-methylimidazole acts both as an acid scavenger and as the solvent. In the second step, chloroform or toluene are preferred, in particular toluene because it is halogen-free.

Although the invention is not limited thereto, during the course of the inventors' research, it was shown that the first step should preferably be carried out at a temperature in the range 100° C. to 200° C., in order to ensure short reaction times, high conversions and good yields. In similar manner, for the second step, temperatures in the range 50° C. to 100° C. have proven advantageous.

The scope of the invention naturally also encompasses the direct products of the method of the invention, i.e. the compounds with formula (I) which are so produced.

Since the tri-substituted melamine, i.e. 2,4,6-tris(9,10-dihydro-9-oxa-10-oxo-10-phosphaphenanthrene-10-ylamino)-1,3,5-triazine ($DOPO_3$-mel):

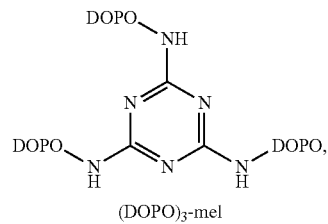

$(DOPO)_3$-mel in which DOPO- is the residue

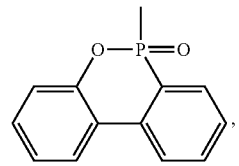

constitutes a novel chemical compound, in a further aspect, the invention pertains to protection of this product as well as to its use as a flame retardant. In the first flammability tests, the inventor shows this novel compound to have an exceptional effect as a flame retardant for plastic materials, in particular for polystyrene and epoxies.

EXAMPLES

The invention will now be described in detail with the aid of the following non-limiting exemplary embodiments.

Example 1

Production of DOPO$_3$-mel, i.e. 2,4,6-tris(9,10-dihydro-9-oxa-10-oxo-10-phosphaphenanthrene-10-ylamino)-1,3,5-triazine

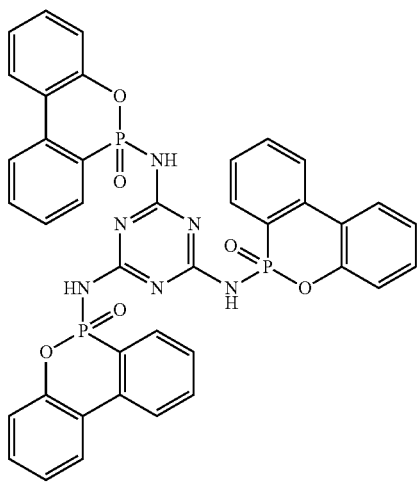 [SMILES: O=P1(Nc2nc(NP3(=O)Oc4ccccc4-c4ccccc43)nc(NP3(=O)Oc4ccccc4-c4ccccc43)n2)Oc2ccccc2-c2ccccc21]

Step 1—Production of DOP$_3$-mel, i.e. 2,4,6-tris(9,10-dihydro-9-oxa-10-phosphaphenanthrene-10-ylamino)-1,3,5-triazine

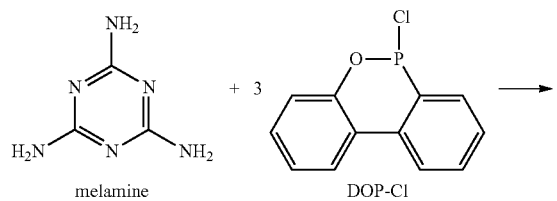

melamine    DOP-Cl

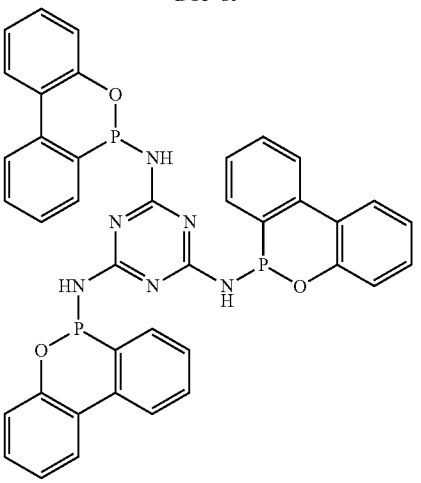

DOP$_3$-mel 12.64 g (0.10 mol) of melamine as well as 82.1 g (1.00 mol) of anhydrous 1-methylimidazole as the acid scavenger and solvent were placed in a three-necked round-bottomed flask filled with argon provided with an integral thermometer, dropping funnel, stirrer and an inert gas feed and heated to 100° C. Next, 72.4 g (0.31 mol) of DOP-Cl was melted at approximately 100° C. under inert conditions and placed in the dropping funnel. The DOP-Cl was dripped in with vigorous stirring over a period of 1 h at 100° C., with the dropping funnel being heated with a hot air blower in order to prevent the reagent from solidifying. Next, stirring was continued for approximately 15 h at 100° C. under argon, after which the viscous contents of the flask were stirred into 500 ml of water and the precipitated granular solid which formed was filtered off through a glass frit. The filter cake was then slaked 2× in 250 ml of water each time and then filtered again. Next, the substance was washed thoroughly with 200 ml of acetone and then rinsed with n-pentane. After drying in a stream of air, 72.4 g of (DOP)$_3$-mel was obtained in a quantitative yield.

$^{31}$P-NMR (101 MHz, DMSO-d$_6$): δ 66.2; 66.1; 65.9 ppm.
$^{1}$H-NMR (250 MHz, DMSO-d$_6$): δ 8.7-8.5 (d, 3H, 3 NH—P); 8.25-8.15 (d, 6H); 7.68-7.53 (t, 6H); 7.50-7.40 (t, 3H), 7.38-7.28 (t, 3H), 7.27-7.17 (t, 3H), 7.08-6.97 ppm (m, 3H).

Step 2—Oxidation of DOP$_3$-mel to Form DOPO$_3$-mel

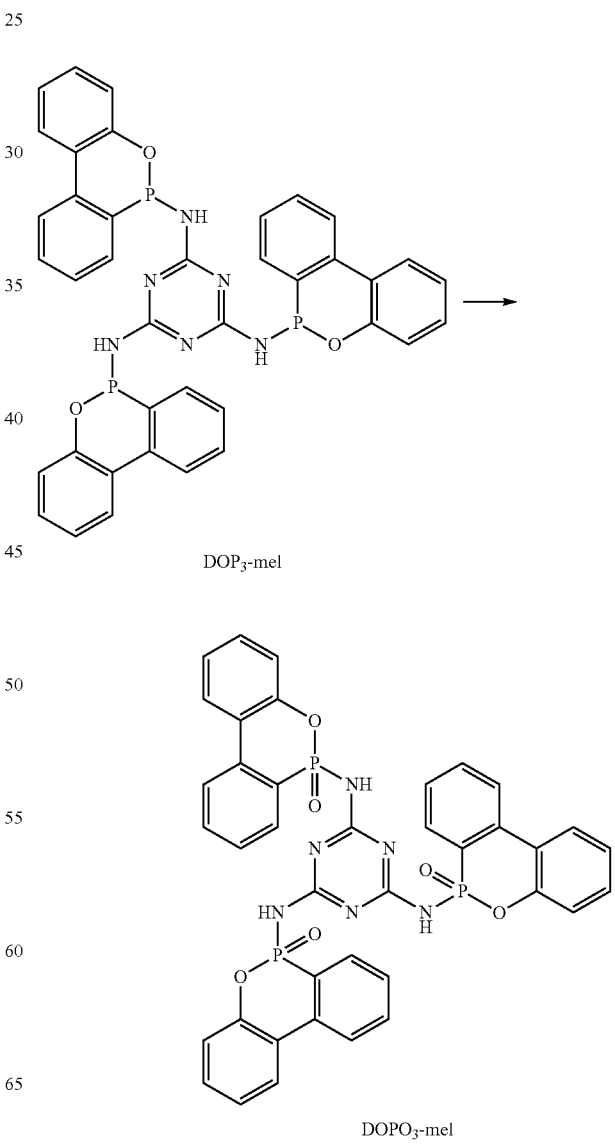

DOPO$_3$-mel

The (DOP)₃-mel (72.4 g) produced in step 1 was stirred at 50° C. into 500 ml of chloroform in a 1-L three-necked flask equipped with a stirrer, integral thermometer and dropping funnel; part of it went up into solution. Next, the mixture was cooled to approximately 12° C. using a cooling bath and addition of an 11% solution of $H_2O_2$ (106.5 g, 34 mol) in acetic acid ethyl ester was immediately commenced. The reagent was dripped in within approximately 1.5 h, with vigorous stirring and with the temperature kept at approximately 15° C. Next, the cooling bath was removed and stirring was continued for a further 2 h. The cloudy solution obtained was supplemented with anhydrous sodium sulphate in order to separate out the water which was formed during the reaction. After filtering the desiccant, the product solution was reduced at 40° C. under a partial vacuum and a crude substance precipitated out. After cooling to approximately 0° C., it was decanted. The remaining solid was slowly heated to 230° C. under vacuum. After approximately 30 min at this temperature, cooling and comminuting the raw product obtained, it was then dissolved in 150 ml of chloroform. This solution was then dripped into 500 ml of diethyl ether with vigorous stirring, whereupon a white, granular solid precipitated out which was filtered off, washed with diethyl ether and dried at 60° C. under vacuum. In this manner, 67 g of (DOPO)₃-mel was obtained (87.2% of theoretical yield).

$^{31}$P-NMR (101 MHz, DMSO-$d_6$): δ 6.86; 6.67; 6.30 ppm.

$^1$H-NMR (250 MHz, DMSO-$d_6$): δ 9.9-9.3 (3H, 3 NH—P); 8.40-8.22 (m, 3H); 8.18-8.00 (t, 6H); 7.78-7.58 (t, 3H), 7.55-7.35 (d, 6H), 7.35-7.16 ppm (m, 6H).

Elemental analysis for $C_{39}H_{27}N_6P_3O_6$ (768.59 g/mol)
calc'd: C, 60.95; H, 3.54; N, 10.93;
found: C, 60.52; H, 3.71; N, 10.80.

Example 2

Production of DOPO₂-Ph guanamine, i.e. 2,4-bis(9,10-dihydro-9-oxa-10-oxo-10-phosphaphenanthrene-10-ylamino)-6-phenyl-1,3,5-triazine

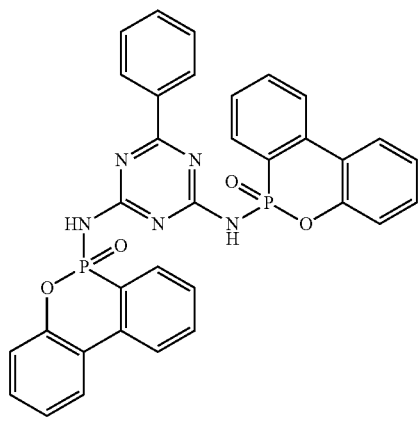 [SMILES: O=P1(Nc2nc(NP3(=O)Oc4ccccc4-c4ccccc43)nc(-c3ccccc3)n2)Oc2ccccc2-c2ccccc21]

Step 1—Production of DOP₂-Ph Guanamine from Phenyl Guanamine and DOP-Cl

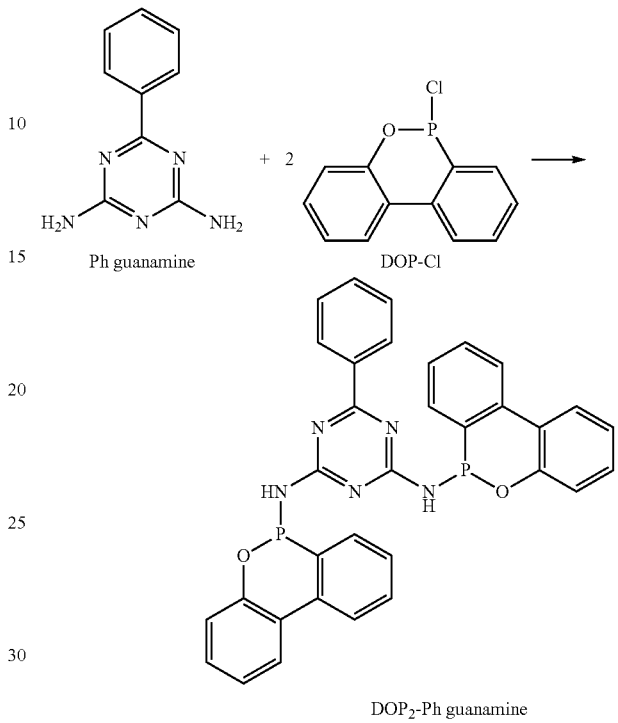

Ph guanamine            DOP-Cl

DOP₂-Ph guanamine 6-phenyl-1,3,5-triazine-2,4-diamine (phenyl guanamine; 33.1 g, 0.177 mol, 1 eq) as well as 1-methylimidazole (145 g, 1.77 mol, 10 eq) were placed in a three-necked flask filled with argon and provided with a condenser, stirrer and dropping funnel. Next, 91.2 g (0.389 mol, 2.2 eq) of DOP-Cl was melted at approximately 100° C. under inert conditions and placed in the dropping funnel. The DOP-Cl was dripped in with vigorous stirring over a period of 1 h at 100° C., wherein a hot air blower was used to keep it liquid. The reaction mixture was kept at this temperature for another 2 h and then stirred into 800 ml of distilled water. The precipitated solid was filtered off and washed 3 times with water and with acetone. Next, the crude product was stirred for 2 h in 300 ml of boiling toluene. The suspension, which was still hot, was filtered and the isolated solid was washed thoroughly with toluene and finally dried in a stream of air. 97.24 g (0.1668 mol, 94.2% of theoretical yield) of (DOP)₂-Ph guanamine was obtained as a white solid.

M.Pt: 276-282° C. (toluene)

$^{31}$P-NMR (101 MHz, DMSO-$d_6$): δ 67.2 ppm (d, J=19.5 Hz, 2P).

$^{13}$C-NMR (63 MHz, DMSO-$d_6$): δ 170.5 (m, 1C, Tr), 167.5 (m, 1C, Tr), 167.2 (m, 1C, Tr), 149.0 (d, J=2.4 Hz, 1C), 148.8 (d, J=2.3 Hz, 1C), 135.5 (s, 1C, Ph), 133.0 (t, J=2.2 Hz, 2C), 132.2 (s, 1C, Ph), 131.4 (s, 2C), 130.9 (d, J=49.2 Hz, 2C—P), 130.4 (m, 2C), 129.5 (s, 2C), 128.4 (s, 2C, Ph), 128.0 (s, 2C, Ph), 127.4 (d, J=13.3 Hz, 2C), 125.6 (s, 2C), 123.8 (s, 2C), 123.5 (d, J=5.7 Hz, 2C), 123.4 (s, 2C), 120.5 ppm (s, 2C).

$^1$H-NMR (250 MHz, DMSO-$d_6$): δ 8.97 (d, J=9.7 Hz, 2H, 2NH—P), 8.35 (d, J=6.8 Hz, 2H), 8.12 (d, J=7.7 Hz, 4H), 7.73-7.63 (m, 4H), 7.63-7.47 (m, 5H), 7.39-7.17 (m, 4H), 7.06 ppm (d, J=6.4 Hz, 2H).

IR (KBr): v 206 (m, N—H), 1540 (vs, O═C—N—H), 1506, 1486, 1424 (vs, P-Ph), 1197 (m, P—O-Ph), 1103, 943, 845, 879, 764 and 746 (s, C—H bend).

HRMS (EI) calc'd for [12C$_{33}$H$_{23}$N$_5$P$_2$O$_2$]+: 583.1327. found: 583.1379 [M]+.

Elemental analysis for C$_{33}$H$_{23}$N$_5$P$_2$O$_2$ (583.52 g/mol)
calc'd: C, 67.93; H, 3.97; N, 12.00; P, 10.62%;
found: C, 67.90; H, 3.93; N, 12.13; P, 10.64%.

Step 2—Oxidation of DOP$_2$-Ph Guanamine to Form DOPO$_2$-Ph Guanamine

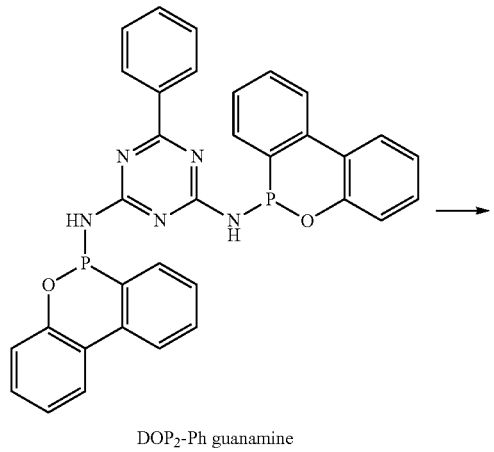

DOP$_2$-Ph guanamine

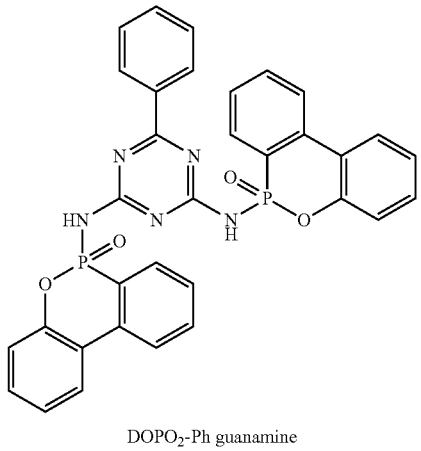

DOPO$_2$-Ph guanamine 11.68 g (0.0020 mol, 1 eq) of (DOP)$_2$-Ph guanamine in 50 ml of chloroform was heated to 40° C. in a three-necked flask equipped with a condenser, stirrer, thermometer and dropping funnel. After 15 min, the mixture was cooled to 20° C. using a cooling bath. Next, 2.88 g (0.048 mol, 2.2 eq) of a 30% aqueous solution of tert-butyl hydroperoxide was slowly dripped in, with vigorous stirring. The vigorous stirring was continued for 1 hour, after which a further 2.00 g (0.033 mol, 1.5 eq) of the oxidizing agent was dripped in. After this, stirring was continued for a further 1 h at ambient temperature and finally, the mixture was filtered. The isolated solid was washed with acetone. An additional fraction of the product was obtained in which the residual solution was reduced under vacuum. The combined fractions were slaked in acetone with vigorous stirring, the suspension was filtered and the solid was dried in a stream of air. In this manner, 11.75 g (0.0019 mol, 95.0% of theoretical yield) of (DOPO)$_2$-Ph guanamine was obtained as a white powder.

M.Pt: 267-273° C. (decomposition.)

$^{31}$P-NMR (101 MHz, DMSO-d$_6$): δ 6.8 (s, 1P), 6.7 ppm (s, 1P).

$^{13}$C-NMR (63 MHz, DMSO-d$_6$): δ 170.3 (s, 1C, Tr), 165.2 (t, J=3.5 Hz, 2C, Tr), 149.7 (d, J=7.4 Hz, 1C), 149.6 (d, J=7.5 Hz, 1C), 135.5 (d, J=7.3 Hz, 2C), 134.1 (s, 1C, Ph), 133.1 (d, J=0.9 Hz, 2C), 132.1 (s, 1C, Ph), 130.5 (s, 2C), 130.3 (m, 2C), 128.5 (d, J=15.1 Hz, 2C), 127.8 (s, 2C, Ph), 127.7 (s, 2C, Ph), 125.2 (s, 2C), 124.5 (s, 2C), 123.8 (d, J=164.3 Hz, 1C—P), 123.7 (d, J=164.3 Hz, 1C—P), 123.5 (d, J=11.5 Hz, 2C), 120.9 (d, J=12.0 Hz, 1C), 120.8 (d, J=12.2 Hz, 1C), 120.0 ppm (m, 2C).

$^{1}$H-NMR (250 MHz, DMSO-d$_6$): δ 10.39 (t, J=8.0 Hz, 2H, 2NH—P), 8.36-8.28 (m, 4H), 8.11-7.88 (m, 2H), 7.70 (t, J=7.4 Hz, 2H), 7.57-7.16 (m, 9H), 7.07-6.87 ppm (m, 4H).

IR (KBr): v 3179 (w, N—H), 1587 (C═C), 1538 (vs, O═C—N—H), 1493, 1454, 1417 (vs, P-Ph), 1232 (s, P═O), 1205 (s, P—O-Ph), 1119, 1088, 943, 876, 751 and 785 (s, C—H bend).

HRMS (EI) calc'd for [12C$_{33}$H$_{23}$N$_5$P$_2$O$_4$]+: 615.1225. found: 615.1290 [M]+.

Elemental analysis for C$_{33}$H$_{23}$N$_5$P$_2$O$_4$ (615.51 g/mol)
calc'd: C, 64.39; H, 3.77; N, 11.38; P, 10.06%;
found: C, 64.07; H, 3.78; N, 11.25; P, 10.16%.

Example 3

Production of DOPO-mel and DOPO$_2$-mel

Step 1—Production of DOP-mel and DOP$_2$-mel

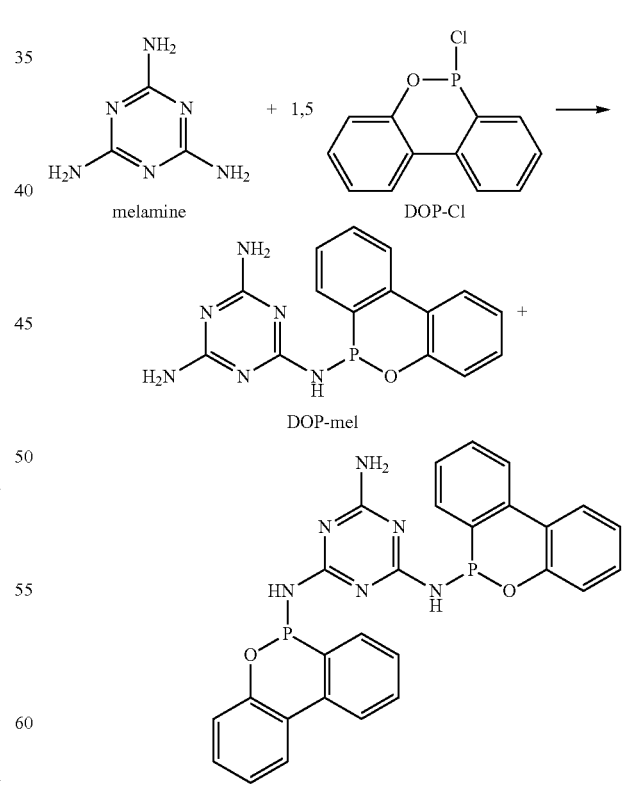

6.31 g (0.050 mol) of melamine as well as 50 g (approximately 0.6 mol) of anhydrous 1-methylimidazole were placed in a 250 ml three-necked round-bottomed flask filled with argon and equipped with an integral thermometer, a dropping funnel, a stirrer as well as an inert gas feed then heated to 100° C. Next, 17.6 g (0.075 mol) of DOP-Cl was melted at 100° C. under inert conditions and placed into the dropping funnel. The DOP-Cl was dripped in with vigorous stirring over 45 min at 100° C.; a hot air blower was used to keep it liquid. After the drip addition was completed, stirring was continued for 3 hours at 120° C. and then for 1 h at 145° C. The $^{31}$P NMR spectrum of the solution obtained showed that DOP-mel and (DOP)$_2$-mel were obtained as the reaction products. This solution was used in the second step at approximately 60° C. without further working-up.

Step 2—Oxidation of DOP-mel and DOP$_2$-mel to Form DOPO-mel and DOPO$_2$-mel

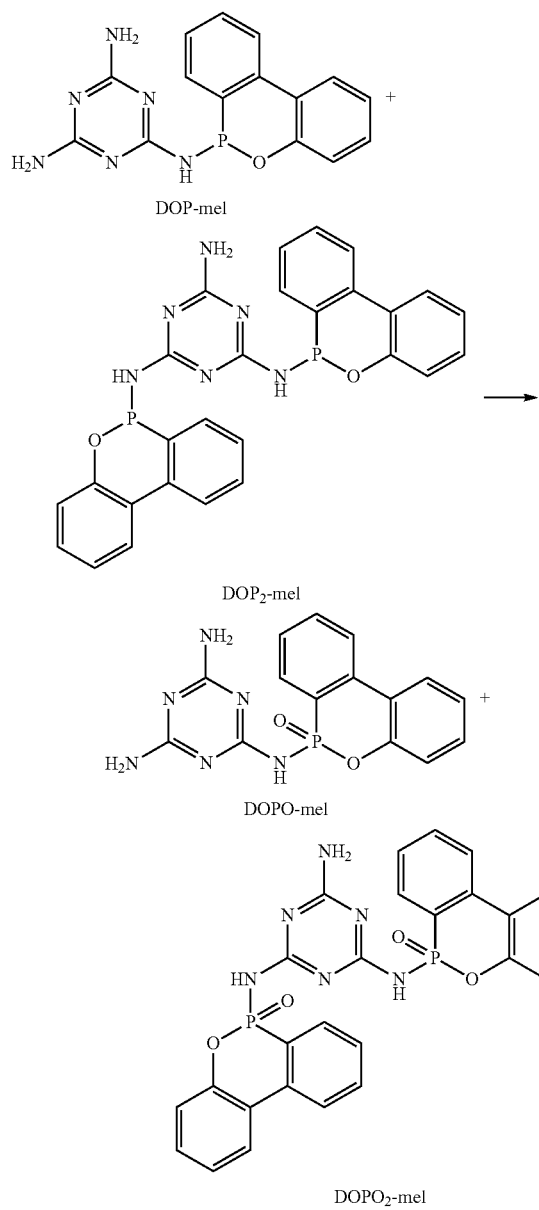

20 g (approximately 0.08 mol) of a 37% solution of tert-butyl hydroperoxide in toluene was dripped onto the mixture of DOP-mel and (DOP)$_2$-mel obtained in step 1 in 1-methylimidazole, at 60-65° C. over 45 min, with stirring. After the reagents had been added, the temperature was maintained at approximately 70° C. for 2 h. Next, the reaction mixture was stirred into 300 ml of water at a temperature of 50° C. After cooling, it was decanted. The substance obtained in this manner was dried for 15 h in a stream of air, comminuted in a mortar and then stirred for 20 min in 300 ml of ethanol under reflux. After cooling to approximately 50° C., it was filtered and the solid was pre-dried at 90° C. under vacuum. Finally, it was heated for approximately 10 h in a vacuum drying cabinet at 170° C. (pressure approximately 12 mbar). The $^1$H and $^{31}$P NMR spectra of the product showed a total quantity of about 98% of DOPO-mel and (DOP)$_2$-mel in a molar ratio of around 1:1.

$^{31}$P-NMR (101 MHz, DMSO-d$_6$): δ 8.79 ppm (DOPO-mel); 7.60; 7.42 ppm ((DOPO)$_2$-mel).

$^1$H-NMR (250 MHz, DMSO-d$_6$): δ 9.8-9.1 (NH—P); 8.15-8.03; 7.8-7.6; 7.55-7.45; 7.45-7.25; 7.25-7.2; 6.8-5.7 (NH$_2$).

MS (ESI): 341 (DOPO-mel, M+1); 555 ((DOPO)$_2$-mel, M+1).

Example 4

Production of DPhPO$_2$-Ph guanamine, i.e. 2,4-bis(diphenylphosphoryl)-6-phenyl-1,3,5-triazine

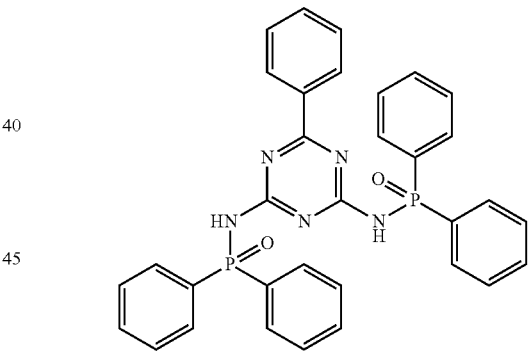

Step 1—Production of DPhP$_2$-Ph Guanamine from Phenylguanamine and DPhP-Cl

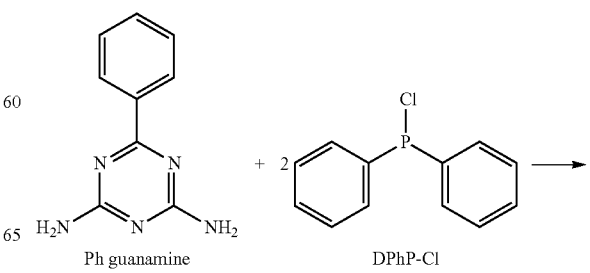

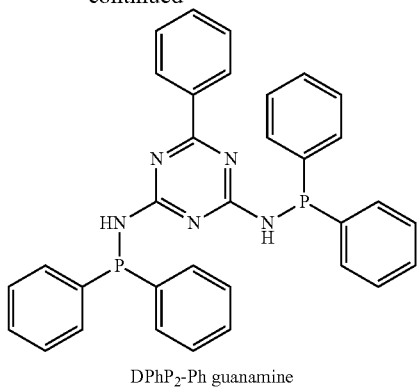

DPhP$_2$-Ph guanamine

Phenyl guanamine (2.38 g, 0.0127 mol, 1 eq), 1-methylimidazole (2.29 g, 0.0279 mol, 2.2 eq) as well as 40 ml of anhydrous toluene were placed in a three-necked flask filled with argon equipped with a condenser, thermometer, stirring means and a dropping funnel and heated to 80° C. 6.16 g (0.0279 mol, 2.2 eq) of diphenylphosphinyl chloride (DPHP-Cl) was slowly dripped in at this temperature, with stirring. Next, the reaction mixture, which was now in two phases, was stirred for 2 h at 90° C. Next, the upper phase was decanted under inert conditions from the viscous lower phase (1-methylimidazolium chloride) and transferred via a connecting piece into a second three-necked flask which had also been filled with argon. In this manner, a solution of DPhP$_2$-Ph guanamine was obtained, which was used in the second step without further working-up.

Step 2—Oxidation of DPhP$_2$-Ph Guanamine to Form DPhPO$_2$-Ph Guanamine

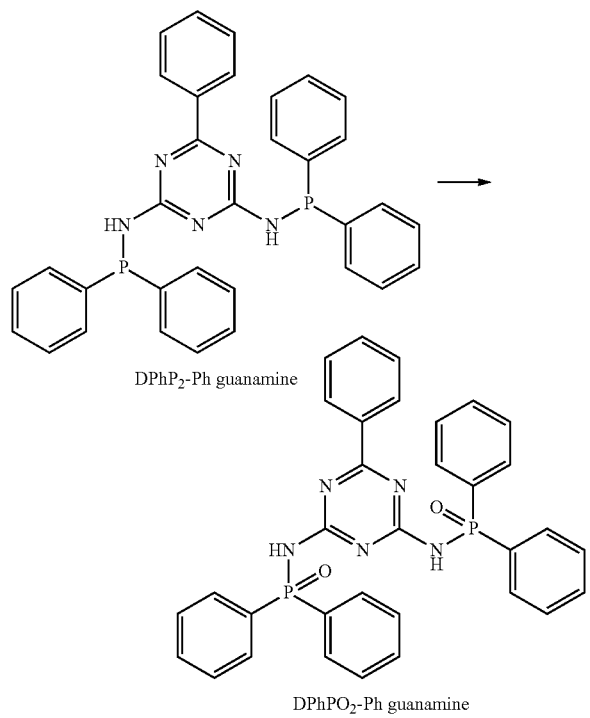

DPhP$_2$-Ph guanamine

DPhPO$_2$-Ph guanamine

The three-necked flask with the solution of DPhP$_2$-Ph guanamine produced in step 1 was equipped with a condenser, thermometer, stirrer and a dropping funnel which had been filled with 6.86 g (0.0381 mol, 3 eq) of an 11% solution of H$_2$O$_2$ in acetic acid ethyl ester. Next, the reaction mixture was cooled to approximately 5° C. using an ice water bath and the oxidizing agent was dripped in slowly and with vigorous stirring, with the temperature being maintained at a maximum of 15° C. After H$_2$O$_2$ addition was complete, the cooling bath was removed and the reaction mixture was stirred for a further 15 h. The precipitated solid was filtered off, washed with toluene and then stirred for 1.5 h in 50 ml of boiling toluene. Next, the hot suspension was filtered and the solid was again washed with toluene and finally dried under vacuum (20 h, 150° C.). In this manner, 5.64 g (0.0096 mol, 75.6% of theoretical yield) of DPhPO$_2$-Ph guanamine was obtained as a white solid.

$^{31}$P-NMR (101 MHz, DMSO-d$_6$): δ 16.1 ppm.
$^1$H-NMR (250 MHz, DMSO-d$_6$): δ 9.89 (d, J=10.2 Hz, 2H, 2NH), 7.85 (m, 8H), 7.50 ppm (m, 14H), 7.15 ppm (m, 3H).
HRMS (EI) calc'd for [12C$_{33}$H$_{27}$N$_5$P$_2$O$_2$]+: 586.1562. found: 586.1656 [M-H]+.

Example 5

Flame Retardant Action Measurements

An epoxy novolac resin, D.E.N. 438 from Dow Chemicals with an EEW (epoxy equivalent weight) of 179 g/mol was mixed with 0.1% by weight of triethanolamine and the novel compound of the invention, DOPO$_3$-mel, as the flame retardant additive—in the amount required to adjust it to the required phosphorus content in the test specimen. The mixture was then maintained for 2 h at 140° C., degassed under vacuum and cooled to 90° C. The pre-formulation obtained was mixed with 6 parts by weight of dicyandiamide and 2 parts by weight of fenuron, referred to 100 parts by weight of epoxy novolac resin. Curing was carried out in an aluminium cup by carefully heating to 120° C. over 30 min, holding this temperature for 1 h, increasing the temperature to 130° C. for 1 h and then holding the temperature at 200° C. for 2 h. 70×13×4 mm test specimens were made from it and classified in accordance with UL94 in order to characterize the flammability.

UL94 is a test protocol from Underwriters Laboratories which has been incorporated in its entirety into IEC/DIN EN 60695-11-10 and -20. In it, igniting flames with a power of 50 W are twice briefly applied to the test specimens, wherein a vertical test of the burn time and drips of flaming particles was assessed with the aid of a pad of cotton wool disposed below the test specimen. The classification categories are "V0", "V1" and "V2" which are explained in Table 1 below:

TABLE 1

UL94 CLASSIFICATION

| Classification | V0 | V1 | V2 |
| --- | --- | --- | --- |
| Burn time after each ignition | ≤10 s | ≤30 s | ≤30 s |
| Total burn time per set (10 ignitions) | ≤50 s | ≤250 s | ≤250 s |
| Burn/glow time after second ignition | ≤30 s | ≤60 s | ≤60 s |
| Combustion up to holder | no | no | no |
| Ignition of cotton | no | no | yes |

The classification "V0" thus constitutes the highest category of flame retardant and thus is the goal for flame retardant compositions.

Table 2 below shows the results of the test for DOPO$_3$-mel and for DOPO as a comparative substance.

TABLE 2

| Flame retardant additive | Phosphorus content (wt %) | UL94 classification |
|---|---|---|
| — | 0.0 | Not classified |
| Comp: DOPO | 1.0 | Not classified |
| Comp: DOPO | 1.4 | V1 |
| Comp: DOPO | 1.6 | V0 |
| Inv: DOPO$_3$-mel | 1.0 | V1 |
| Inv: DOPO$_3$-mel | 1.4 | V0 |

These results clearly show the improved flame retardant action of DOPO$_3$-mel compared with the commercially available additive DOPO. Thus, the new compound DOPO$_3$-mel is highly suitable as a flame retardant in plastics materials.

What is claimed is:

1. A method for producing a compound with the following formula (I):

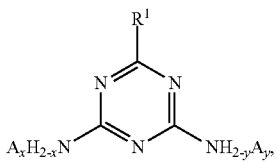

wherein:
the residue $R^1$ is selected from —NH$_2$, —NH$_{2-z}$A$_z$ as well as monovalent alkyl and aryl residues,
the residues A are each selected, independently of each other, from the following phosphoryl residues DOPO-, DPhPO- and DPhOPO-:

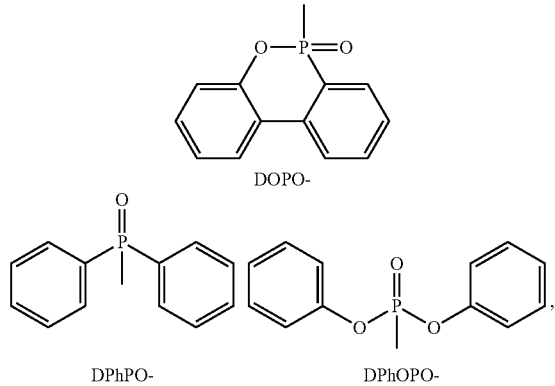

and
the indices x, y and z each, independently of each other, represent 0 or 1, wherein at least one of the indices ≠0;
in which, in a first step, melamine or, when $R^1$ is an alkyl or aryl residue, the corresponding alkyl or aryl guanamine is reacted with one of the following phosphinyl chlorides DOP-Cl, DPhP-Cl and DPhOP-Cl:

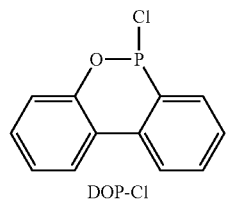

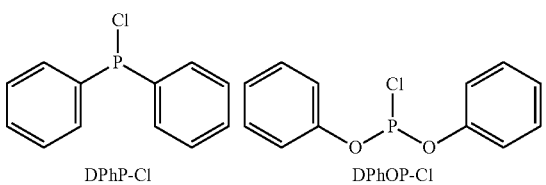

in order to bind one or more phosphinyl residue(s) to the amino group(s) of the melamine or guanamine, after which in a second step, the bound phosphinyl residue(s) is(are) oxidized by reaction with an oxidizing agent to form the corresponding phosphoryl residue(s).

2. The method as claimed in claim 1, characterized in that the monovalent alkyl or aryl residue of $R^1$ is selected from —CH$_3$ and —C$_6$H$_5$.

3. The method as claimed in claim 1, characterized in that a peroxide is used as the oxidizing agent.

4. The method as claimed in claim 1, characterized in that hydrogen peroxide or t-butyl hydroperoxide is used as the oxidizing agent.

5. The method as claimed in claim 1, characterized in that the first step is carried out in the presence of an acid scavenger.

6. The method as claimed in claim 5, characterized in that the acid scavenger simultaneously functions as a solvent.

7. The method as claimed in claim 5, characterized in that 1-methylimidazole is used as the acid scavenger and solvent.

8. The method as claimed in claim 1, characterized in that the second step is carried out in an organic solvent selected from chloroform and toluene.

9. The method as claimed in claim 1, characterized in that the first step is carried out at a temperature in the range 100° C. to 200° C.

10. The method as claimed in claim 1, characterized in that the second step is carried out at a temperature in the range 50° C. to 100° C.

11. 2,4,6-tris(9,10-dihydro-9-oxa-10-oxo-10-phosphaphenanthrene-10-ylamino)-1,3,5-triazine (DOPO$_3$-mel):

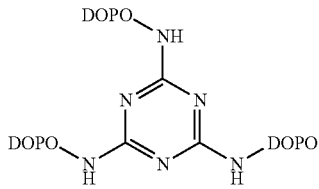

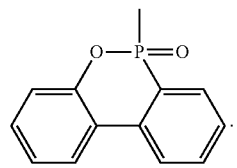
wherein DOPO- corresponds to the residue.
12. A process of making a flame retardant 2,4,6-tris(9,10-dihydro-9-oxa-10-oxo-10-phosphaphenanthrene-10-ylamino)-1,3,5-triazine comprising: first, reacting melamine with phosphinyl chloride DOP-Cl, and then, oxidizing the bound phosphinyl residue with an oxidizing agent to make said flame retardant.
* * * * *